US007008936B2

(12) United States Patent
Voi et al.

(10) Patent No.: US 7,008,936 B2
(45) Date of Patent: Mar. 7, 2006

(54) COMBINATION OF EPOTHILONE ANALOGS AND CHEMOTHERAPEUTIC AGENTS FOR THE TREATMENT OF PROLIFERATIVE DISEASES

(75) Inventors: Maurizio Voi, Bruxelles (BE); David Lebwohl, Madison, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/459,972

(22) Filed: Jun. 12, 2003

(65) Prior Publication Data

US 2004/0024032 A1 Feb. 5, 2004

Related U.S. Application Data

(60) Provisional application No. 60/388,702, filed on Jun. 14, 2002.

(51) Int. Cl.
A61K 31/555 (2006.01)
A61K 31/425 (2006.01)
A61K 31/28 (2006.01)
(52) U.S. Cl. .................... 514/184; 514/365; 514/492
(58) Field of Classification Search ................ 514/183, 514/203, 210.02, 291, 365, 450, 492
See application file for complete search history.

(56) References Cited

U.S. PATENT DOCUMENTS

| 6,103,487 | A * | 8/2000 | Barnett et al. ............... 435/15 |
| 6,194,181 | B1 | 2/2001 | Hofmann et al. |
| 6,204,388 | B1 | 3/2001 | Danishefsky et al. |
| 6,211,412 | B1 | 4/2001 | Georg et al. |
| 6,242,469 | B1 | 6/2001 | Danishefsky et al. |
| 6,316,630 | B1 | 11/2001 | Danishefsky et al. |
| 6,365,749 | B1 | 4/2002 | Kim et al. |
| 6,369,234 | B1 | 4/2002 | Danishefsky et al. |
| 6,380,227 | B1 | 4/2002 | Mutz |
| 6,399,638 | B1 | 6/2002 | Vite et al. |
| 2003/0073677 | A1 * | 4/2003 | Lee ............................ 514/183 |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |

OTHER PUBLICATIONS

Cecil, Textbook of Medicine, 21$^{st}$ ed., vol. 1, published 2000 by W.B Saunders Company (PA), pp 1060-74.*
U.S. Appl. No. 08/856,533, filed May 14, 1997, Nicolaou, et al.
U.S. Appl. No. 08/923,869, filed Sep. 4, 1997, Nicolaou, et al.
U.S. Appl. No. 60/032,864, filed Dec. 13, 1996, Nicolaou, et al.
Balog, A., et al., "Total Synthesis of (-)-Epothilone A", *Angew. Chem. Int. Ed. Engl.*, vol. 35, No. 23/24, 2801-2803 (1996).
Bertini, F., et al., "Aikenes from Epoxides by Reductive Elimination with Magnesium Bromide-Magnesium Amalgam", *Chem. Commun.*, 144 (1970).
Bollag, D.M., et al., "Epothilones, A New Class of Microtubule-stabilizing Agents with a Taxol-like Mechanism of Action", *Cancer Res.* 55, No. 11, 2325-2333 (1995).
Fujisawa, T., et al., "Deoxygenation of Epoxides to Olefins with FeCl$_3$—n-BuLi System", *Chem. Lett.*, 883-886 (1974).
Fujiwara, Y., et al., "Reductive Coupling of Carbonyl Compounds to Olefins by Tungsten Hexachloride-Lithium Aluminum Hydride and Some Tungsten and Molybdenum Carbonyls", *J. Org. Chem.*, vol. 43, No. 12, 2477-2479 (1978).
Gladysz, J. A., et al., "Deoxygenation of Epoxides by Metal Atom Cocondensation", *J. Org. Chem.*, vol. 41, No. 22, 3647-3648 (1976).

(Continued)

*Primary Examiner*—Raymond J. Henley, III
(74) *Attorney, Agent, or Firm*—Anastasia P. Winslow

(57) ABSTRACT

Compositions and methods are disclosed which are useful of the treatment and prevention of proliferative diseases.

8 Claims, No Drawings

OTHER PUBLICATIONS

Hofle, G., et al., "Epothilone A and B—Novel 16-Membered Macrolides with Cytotoxic Activity: Isolation, Crystal Structure, and Conformation in Solution", *Angew. Chem. Int. Ed. Engl.*, vol. 35, No. 13/14, 1567-1569 (1996).

Hofle, G., et al., "N-Oxidation of Epothilone A-C and O-Acyl Rearrangement to C-19 and C-21 -Substituted Epothilones", *Angew. Chem. Int. Ed.*, vol. 38, No. 13/14, 1971-1974 (1999).

Inokuchi, T., et al., "Opening of Epoxides to Olefins or Halohydrins with Vanadium(II)-Tetrahydrofuran or Vanadium(III)-Tetrahydrofuran Complexes", *Synlett*, No. 6, 510-512 (1992).

Kowalski. R. J., et al., "Activities of the Microtubule-stabilizing Agents Epothilones A and B with Purified Tubulin and in Cells Resistant to Paclitaxel (Taxol®)" *J. Biol. Chem.*, vol. 272, No. 4, 2534-2541 (1997).

Kupchan, S. M., et al., "Reductive Elimination of Epoxides to Olefins with Zinc-Copper Couple", *J. Org. Chem.*, vol. 36, No. 9, 1187-1190 (1971).

Martin, M. G., et al., "Epoxides as Alkene Protecting Groups. A Mild and Efficient Deoxygenation", *Tetrahedron Letters*, vol. 25, No. 3, 251-254 (1984).

McMurry, J. E., et al., "Reduction of Epoxides to Olefins with Low Valent Titanium", *J. Org. Chem.*, vol. 40, No. 17, 2555-2556 (1975).

McMurry, J. E., "Some Deoxygenation Reactions with Low-Valent Titanium ($TiCl_3$/$LiAlH_4$)", *J. Org. Chem.*, vol. 43, No. 17, 3249-3254 (1978).

Meng, D., et al., "Remote Effects in Macrolide Formation Through Ring-Forming Olefin Metathesis: An Application to the Synthesis of Fully Active Epothilone Congeners", *J. Am. Chem. Soc.*, vol 119, No. 11, 2733-2734 (1997).

Nicolaou, K. C., et al., "An Approach to Epothilones Based on Olefin Metathesis", *Angew. Chem. Int. Ed. Engl.*, vol. 35, No. 20, 2399-2401 (1996).

Nicolaou, K. C., et al., "Total Synthesis of Epothilone A: The Macrolactonization Approach", *Angew. Chem. Int. Ed. Engl.*, vol. 36, No. 5, 525-527 (1997).

Nicolaou, K. C., et. al., "Designed Epothilones: Combinatorial Synthesis, Tubulin Assembly Properties, and Cytotoxic Action against Taxol-Resistant Tumor Cells", *Angew. Chem. Int. Ed. Engl.*, vol. 36, No. 19, 2097-2103 (1997).

Nicolaou, K.C., et al., "The Olefin Metathesis Approach to Epothilone A and Its Analogues", *J. Am. Chem. Soc.*, vol. 119, No. 34, 7960-7973 (1997).

Nicolaou, K. C., et al., "Total Syntheses of Epothilones A and B via a Macrolactonization-Based Strategy", *J. Am. Chem. Soc.*, vol. 119, No. 34, 7974-7991 (1997).

Nicolaou, K. C., et al., "Synthesis of Epothilones A and B in Solid and Solution Phase", *Nature*, vol. 387, 268-272 (1997).

Nicolaou, K. C., et al., "Synthesis of Epothilones A and B in Solid and Solution Phase" (Correction to *Nature* 387, 268-272 (1997)), *Nature*, 390, 100 (1997).

Raucher, S., et al., "Total Synthesis of (+)-Dihydrocostunolide via Tandem Cope-Claisen Rearrangement", *J. Org. Chem.*, vol. 51, No. 26, 5503-5505 (1986).

Sato, M, et al., "Reduction of Organic Compounds with Low-valent Niobium ($NbCl_5$/$NaAlH_4$)", *Chem. Letters*, 157-160 (1982).

Schinzer, D., et al., "Total Synthesis of (-)-Epothilone A", *Angew. Chem. Int. Ed. Engl.*, vol. 36, No. 5, 523-524 (1997).

Schobert, R., et al., "Reduction and Isomerization of Oxiranes and α-Diazoketones by Various Early Transition Metallocenes", *Synlett*, vol. 8, 465-466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538-6540 (1972).

Su, D.-S., et al., "Total Synthesis of (-)-Epothilone B: An Extension of the Suzuki Coupling Method and Insights into Structure-Activity Relationships of the Epothilones", *Angew. Chem. Int. Ed. Engl.*, vol. 36, No. 7, 757-759 (1997).

Su, D.-S., et al., "Structure-Activity Relationships of the Epothilones and the First In Vivo Comparison with Paclitaxel", *Angew. Chem. Int. Ed. Engl.*, vol. 36, No. 19, 2093-2096 (1997).

Victory, S. F., et al., "Relative Stereochemistry and Solution Conformation of the Novel Paclitaxel-Like Antimitotic Agent Epothilone A", *Bioorg. Med. Chem. Letts.*, vol. 6., No. 7, 893-898 (1996).

Winkler, J. D., et al., "A Model For The Taxol (Paclitaxel)/Epothilone Pharmacophore", *Bioorg. Med. Chem. Letts.*, vol. 6, No. 24, 2963-2966 (1996).

Yang, Z., et al., "Total Synthesis of Epothilone A: The Olefin Metathesis Approach", *Angew. Chem. Int. Ed. Engl.*, vol. 36, No. 1/2, 166-168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule-Stabilising Agents", *Expert Opin. Invest. Drugs*, vol. 6, No. 7, 867-873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000-8001 (1996).

*Chemical & Engineering News*, "Epothilone Epiphany: Total Syntheses", vol. 74, No. 52, 24-26 (1996).

*Chemical & Engineering News*, "First Total Synthesis of Epothilone B" , vol. 75, No. 13, 23 (1997).

*Chemical & Engineering News*, "Solid-Phase Epothilone Synthesis Used to Create Analog Library", vol. 75, No. 20, 33 (1997).

Claus, E., et al., "Synthesis of the C1-C9 Segment of Epothilons", *Tetrahedron Lett.*, vol. 38, No. 8, 1359-1362 (1997).

De Brabander, J., et al., "Towards a Synthesis of Epothilone A: Rapid Assembly of the C1-C6 and C7-C12 Fragments", *Synlett*, vol. 7, 824-826 (1997).

Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones", *Tetrahedron Lett.*, vol. 38, No. 8, 1363-1366 (1997).

Gerth, K., et al., "Epothilons A and B: Antifungal and Cytotoxic Compounds from *Sorangiusm cellulosum* (Myxobacteria) Production, Physico-chemical and Biological Properties", *J. Antibiotics*, vol. 49, No. 6, 560-563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998-7999 (1996).

Meng, D., et al., "Total Syntheses of Epothilones A and B", *J. Am. Chem. Soc.*, vol. 119, No. 42, 10073-10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96-97 (1997).

Mulzer, J. and Mantoulidis, A., "Synthesis of the C(1)-C(9) Segment of the Cytotoxic Macrolides Epothilon A and B", *Tetrahedron Lett.*, vol. 37, No. 51, 9179-9182 (1996).

Nicolaou, K., et al., "Chemistry, Biology and Medicine of Selected Tubulin Polymerizing Agents", *Pure Appl. Chem.*, vol. 71, No. 6, 989-997 (1999).

Nicolaou, K., et al., "Total Synthesis of Epothilone E and Related Side-chain Modified Analogues Via a Stille Coupling Based Strategy", *Bioorg. Med. Chem.*, vol. 7, No. 5, 665-697 (1999).

Schinzer, D., et al., "Studies Toward the Total Synthesis of Epothilones: Asymmetric Synthesis of the Key Fragments", *Chem. Eur. J.*, vol. 2, No. 22, 1477-1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061-2064 (1997).

Schinzer, D., et al., "Syntheses of (-)-Epothilone A", *Chem. Eur. J.*, vol. 5, No. 9, 2483-2491 (1999).

Schinzer, D., et al., "Syntheses of (-)-Epothilone B", *Chem. Eur. J.*, vol. 5, No. 9, 2492-2500 (1999).

Nicolaou, K. C., et al., "Synthesis and Biological Properties of C12, 13-Cyclopropylepothilone A and Related Epothilones", *Chemistry & Biology*, vol. 5, No. 7, 365-372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84-87 (1998).

Nicolaou et al., "Total Synthesis of Oxazole- and Cyclopropane-Containing Epothilone B Analogues by the Macrolactonization Approach", Chemistry, European Journal, vol. 3, No. 12, 1971-1986 (1997).

Nicolaou et al., "Chemical Biology of Epothilones", Angew. Chem. Int. Ed., 37, 2014-2045 (1988).

* cited by examiner

COMBINATION OF EPOTHILONE ANALOGS AND CHEMOTHERAPEUTIC AGENTS FOR THE TREATMENT OF PROLIFERATIVE DISEASES

CROSS-REFERENCE TO RELATED APPLICATIONS

This application claims priority from provisional U.S. Application Ser. No. 60/388,702, filed on Jun. 14, 2002, incorporated herein by reference in its entirety.

FIELD OF THE INVENTION

This invention relates to the fields of oncology and improved chemotherapy regimens.

BACKGROUND OF THE INVENTION

The disclosure of each literature article and published patent document referred to herein is incorporated by reference in its entirety.

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromastase inhibitors, bifunctional alkylating agents, etc.

Paclitaxel represents one of the major classes of antimicrotubule agents that promotes tubulin polymerization and, presumably, mitotic arrest during cell division. Taxol (paclitaxel) has been shown to have excellent antitumor activity in vivo and has been employed in the treatment of a variety of cancers, including breast, ovarian and lung cancer. Unfortunately, many tumors develop resistance to paclitaxel.

Epothilones mimic the biological effects of taxol, (Bollag et al., Cancer Research 55: 2325–2333 (1995), and in competition studies act as competitive inhibitors of taxol binding to microtubules. However, epothilones enjoy a significant advantage over taxol in that epothilones exhibit a much lower drop in potency compared to taxol against a multiple drug-resistant cell line (Bollag et al. (1995)). Furthermore, epothilones are considerably less efficiently exported from the cells by P-glycoprotein than is taxol (Gerth et al. (1996)).

It is an object of the invention to provide efficacious combination chemotherapeutic treatment regimens wherein epothilone analogs are combined with other anti-neoplastic agents for the treatment of proliferative diseases.

SUMMARY OF THE INVENTION

The present invention provides a method for the treatment of anti-proliferative diseases, including cancer, which comprises administering to a mammalian specie in need thereof, a therapeutically effective amount of: (1) a compound of formula I and (2) at least one anti-proliferative agent.

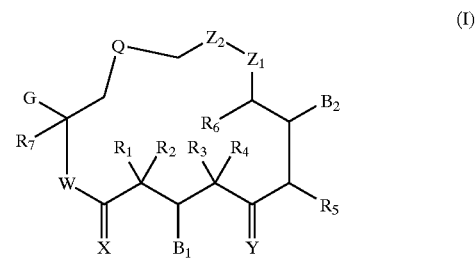

(I)

wherein:

Q is selected from the group consisting of

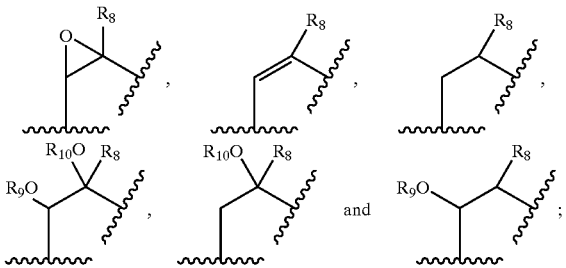

G is selected from the group consisting of alkyl, substituted alkyl, aryl, substituted aryl, heterocyclo,

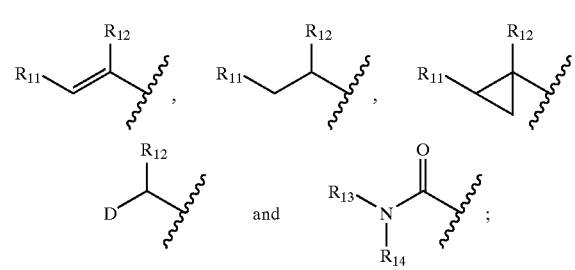

W is O or N $R_{15}$;

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently selected from the group consisting of $CH_2$, O, $NR_{23}$, S, and $SO_2$, wherein only one of $Z_1$ and $Z_2$ can be a heteroatom;

$B_1$ and $B_2$ are independently selected from the group consisting of $OR_{24}$, $OCOR_{25}$, and O—C(=O)—$NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

$R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_9$, $R_{10}$, $R_{16}$, $R_{17}$, $R_{24}$, $R_{25}$ and $R_{31}$ are independently selected from the group consisting of H, alkyl, and substituted alkyl;

$R_8$, $R_{11}$, $R_{12}$, $R_{28}$, $R_{30}$, $R_{32}$, and $R_{33}$ are independently selected from the group consisting of H, alkyl, substituted alkyl, aryl, substituted aryl, cycloalkyl and heterocyclo;

$R_{15}$, $R_{23}$ and $R_{29}$ are independently selected from the group consisting of H, alkyl, substituted alkyl, aryl, substituted aryl, cycloalkyl, heterocyclo, $R_{32}C=O$, $R_{33}SO_2$, hydroxy, O-alkyl or O-substituted alkyl; and pharmaceutically acceptable salts thereof and any hydrates, solvates or geometric, optical and steroisomers thereof.

An example of a compound of Formula I is the compound of Formula Ia ("Compound 1"):

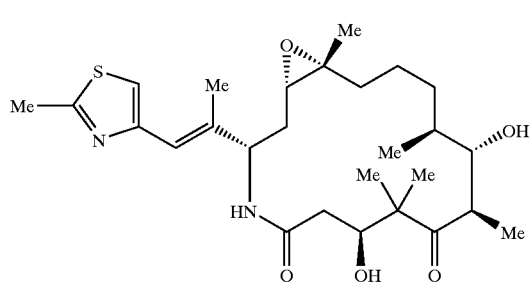

Ia

Suitable anti-proliferative agents for use in the methods of the invention, include, without limitation, alkylating agents (including, without limitation, nitrogen mustards, ethylenimine derivatives, alkyl sulfonates, nitrosoureas and triazenes): Uracil mustard, Chlormethine, Cyclophosphamide (Cytoxan), Carboplatin, Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; antimetabolites (including, without limitation, folic acid antagonists, pyrimidine analogs, purine analogs and adenosine deaminase inhibitors), Methotrexate, 5-Fluorouracil, Floxuridine, Cytarabine, 6-Mercaptopurine, 6-Thioguanine, Fludarabine phosphate, Pentostatine, and Gemcitabine; natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; navelbene, CPT-11, anastrazole, letrazole, capecitabine, reloxafine, cyclophosphamide, ifosamide, and droloxafine and radiation.

According to the present invention, the antiproliferative agent is administered prior to, simultaneously with, or after the administration of a compound of Formula I, such as the compound of Formula Ia.

DETAILED DESCRIPTION OF THE INVENTION

In accordance with the present invention, methods for the scheduled administration of epothilone analogs in combination(s) with at least one additional anti-neoplastic agent for the treatment and prevention of proliferative diseases are provided.

Epothilones mimic the biological effects of taxol, (Bollag et al., Cancer Research 55: 2325–2333 (1995), and in competition studies act as competitive inhibitors of taxol binding to microtubules. However, epothilones enjoy a significant advantage over taxol in that epothilones exhibit a much lower drop in potency compared to taxol against a multiple drug-resistant cell line (Bollag et al. (1995)). Furthermore, epothilones are considerably less efficiently exported from the cells by P-glycoprotein than is taxol (Gerth et al. (1996)).

In one embodiment of the present invention, the chemotherapeutic method of the invention comprises the administration of an epothilone analog of Formula I in combination with at least one other anti-cancer or anti-proliferative agent. The epothilone analogs disclosed herein, when used in combination with at least one other anti-cancer agent, demonstrate superior cytotoxic activity.

Epothilone analogs for use in the methods of the invention are compounds of Formula I:

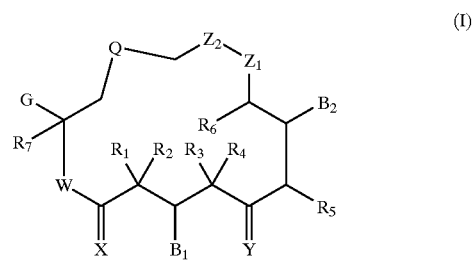

(I)

wherein:

Q is selected from the group consisting of

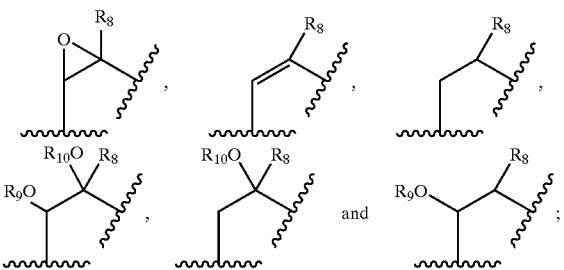

G is selected from the group consisting of alkyl, substituted alkyl, aryl, substituted aryl, heterocyclo,

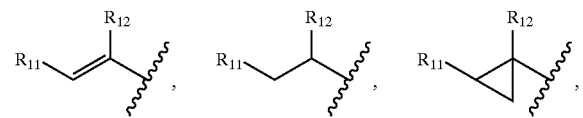

-continued

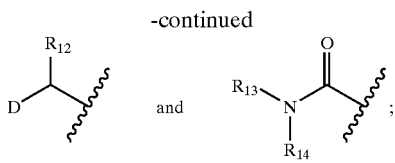

and

W is O or $NR_{15}$;

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently selected from the group consisting of $CH_2$, O, $NR_{23}$, S, and $SO_2$, wherein only one of $Z_1$ and $Z_2$ can be a heteroatom;

$B_1$ and $B_2$ are independently selected from the group consisting of $OR_{24}$, $OCOR_{25}$, and O—C(=O)—$NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

$R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_9$, $R_{10}$, $R_{16}$, $R_{17}$, $R_{24}$, $R_{25}$ and $R_{31}$ are independently selected from the group consisting of H, alkyl, and substituted alkyl;

$R_8$, $R_{11}$, $R_{12}$, $R_{28}$, $R_{30}$, $R_{32}$, and $R_{33}$ are independently selected from the group consisting of H, alkyl, substituted alkyl, aryl, substituted aryl, cycloalkyl and heterocyclo;

$R_{15}$, $R_{23}$ and $R_{29}$ are independently selected from the group consisting of H, alkyl, substituted alkyl, aryl, substituted aryl, cycloalkyl, heterocyclo, $R_{32}C$=O, $R_{33}SO_2$, hydroxy, O-alkyl or O-substituted alkyl; and pharmaceutically acceptable salts thereof and any hydrates, solvates or geometric, optical and steroisomers thereof.

According to the present invention, the anti-proliferative agent may be administered prior to, simultaneously with, or after the administration of an epothilone analog of Formula I.

Examples of compounds of Formula I include [1S 1R*, 3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17oxabicyclo[14.1.0]-heptadecane-5,9-dione (Formula Ia; Compound 1) and pharmaceutically acceptable salts thereof. Compound 1 has the following chemical structure:

Ia

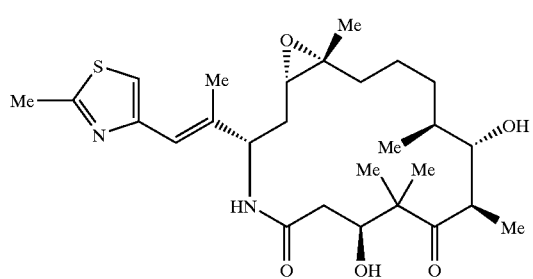

When describing the compounds of the present invention, the phrase "lower alkyl" or "lower alk" (as part of another group) refers to an unsubstituted alkyl group of 1 to 6, such as 1 to 4, carbon atoms.

The term "aralkyl" refers to an aryl group bonded directly through a lower alkyl group. An example of an aralkyl group is benzyl.

The term "aryl" refers to a monocyclic or bicyclic aromatic hydrocarbon group having 6 to 12 carbon atoms in the ring portion. Exemplary of aryl herein are phenyl, naphthyl and biphenyl groups.

The term "heterocyclo" refers to a fully saturated or unsaturated, aromatic or nonaromatic cyclic group which is a 4 to 7 membered monocyclic, 7 to 11 membered bicyclic, or 10 to 15 membered tricyclic ring system which has at least one heteroatom in at least one carbon atom-containing ring. Each ring of the heterocyclic group containing a heteroatom may have 1, 2, 3 or 4 heteroatoms selected from nitrogen, oxygen and sulfur where the nitrogen and sulfur heteroatoms may also optionally be oxidized and the nitrogen heteroatoms may also optionally be quaternized. The heterocyclo group may be attached at any heteroatom or carbon atom.

Exemplary monocyclic heterocyclo groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolinyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclo groups include benzothiazolyl, benzoxazolyl, benzothienyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

When a group is referred to as being optionally substituted, it may be substituted with one to five, preferably one to three, substituents such as F, Cl, Br, I, trifluoromethyl, trifluoromethoxy, hydroxy, lower alkoxy, cycloalkoxy, heterocyclooxy, oxo, lower alkanoyl, aryloxy, lower alkanoyloxy, amino, lower alkylamino, arylamino, aralkylamino, cycloalkylamino, heterocycloamino, disubstituted amines in which the two amino substituents independently are selected from lower alkyl, aryl or aralkyl, lower alkanoylamino, aroylamino, aralkanoylamino, substituted lower alkanoylamino, substituted arylamino, substituted aralkylanoylamino, thiol, lower alkylthio, arylthio, aralkylthio, cycloalkylthio, heterocyclothio, lower alkylthiono, arylthiono, aralkylthiono, lower alkylsulfonyl, arylsulfonyl, aralkylsulfonyl, sulfonamide (e.g., SO$_2$NH$_2$), substituted sulfonamide, nitro, cyano, carboxy, carbamyl (e.g., CONH$_2$), substituted carbamyl (e.g., CONH-lower alkyl, CONH-aryl, CONH-aralkyl or cases where there are two substituents on the nitrogen independently selected from lower alkyl, aryl or aralkyl), lower alkoxycarbonyl, aryl, substituted aryl, guanidino, and heterocyclos (e.g., indolyl, imidazolyl, furyl, thienyl, thiazolyl, pyrrolidyl, pyridyl, pyrimidyl and the like). Where noted above that the substitutuent is further substituted, it will be substituted with F, Cl, Br, I, optionally substituted lower alkyl, hydroxy, optionally substituted lower alkoxy, optionally substituted aryl, or optionally substituted aralkyl.

All stereoisomers of the Formula I compounds of the instant invention are contemplated, either in admixture or in pure or substantially pure form. The definition of the formula I compounds embraces all possible stereoisomers and their mixtures. The Formula I definitions very particularly embrace the racemic forms and the isolated optical isomers having the specified activity.

An example of an epothilone analog of Formula I for use in the methods of the invention is Compound 1: [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl) ethenyl]-4-aza-17-oxabicyclo[14.1.0]heptadecane-5,9-dione. Compound 1 is described in WO 99/02514, published Jan. 21, 1999, the entire contents of which are herein incorporated by reference.

Compound 1, an exemplary epothilone analog of the invention, is a semi-synthetic epothilone analog and has a mode of action analogous to paclitaxel (i.e., microtubule stabilization). However, in preclinical pharmacology studies, Compound 1 has demonstrated significant improvement over paclitaxel in several critical aspects. Compound 1 exhibits a very impressive and broad spectrum of antitumor activity against paclitaxel-sensitive (A2780, HCT116 and LS174T) and, more importantly, as well as paclitaxel-resistant human colon tumors (HCT116/VM46), ovarian carcinoma (Pat-7 and A2780Tax) and breast carcinoma (Pat-21) models. Compound 1 is orally efficacious; the antitumor activity produced after oral administration is comparable to that produced by parenteral administration of the drug. These preclinical efficacy data indicate that Compound 1 demonstrates improved clinical efficacy in TAXOL®-insensitive and sensitive disease types.

As used herein, the phrase "anti-neoplastic agent" is synonymous with "chemotherapeutic agent" and/or "anti-proliferative agent" and refers to compounds that prevent cancer, or hyperproliferative cells, from multiplying. Anti-proliferative agents prevent cancer cells from multiplying by: (1) interfering with the cell's ability to replicate DNA and (2) inducing cell death and/or apoptosis in the cancer cells.

Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxycoformycin, Mitomycin-C, L-Asparaginase, Interferons (especially IFN-a), Etoposide, and Teniposide.

Other anti-proliferative cytotoxic agents are navelbene, CPT-11, anastrazole, letrazole, capecitabine, carboplatin, reloxafine, cyclophosphamide, ifosamide, and droloxafine.

The phrase "radiation therapy" includes, but is not limited to, x-rays or gamma rays which are delivered from either an externally applied source such as a beam or by implantation of small radioactive sources.

Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including, but not limited to, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in WO 99/02514, published Jan. 21, 1999, entire contents of which are herein incorporated by reference), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Pat. No. 6,262,094, issued Jul. 17, 2001, entire contents of which are herein incorporated by reference, and examples 7 and 8 therein), and derivatives thereof; and other microtubule disruptor agents. Additional antineoplastic agents include discodermolide (see Service, (1996) Science, 274:2009) estramustine, nocodazole, MAP4, and the like. Examples of such agents are also described in the scientific and patent literature, see, e.g., Bulinski (1997) *J. Cell Sci.* 110:3055 3064; Panda (1997) *Proc. Natl. Acad. Sci. USA* 94:10560–10564; Muhlradt (1997) Cancer Res. 57:3344–3346; Nicolaou (1997) *Nature* 387:268–272; Vasquez (1997) *Mol. Biol. Cell.*8:973–985; Panda (1996) *J. Biol. Chem* 271:29807–29812.

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex™ which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. One exemplary class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Thus, the present invention provides methods for the treatment of a variety of cancers including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, in one embodiment, the invention is used to treat accelerated or metastatic cancers, such as bladder cancer, pancreatic cancer, prostate cancer, non-small cell lung cancer, colorectal cancer and breast cancer.

In another embodiment of this invention, methods are provided for the treatment of cancerous tumors. Advantageously, the method of this invention reduces the development of tumors, reduces tumor burden, or produces tumor regression in a mammalian host.

Methods for the safe and effective administration of most of these chemotherapeutic agents are known to those skilled in the art. In addition, their administration is described in the standard literature.

For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

The Formula I compounds may be prepared by the procedures described in WO 99/02514, published Jan. 21, 1999.

The compounds of Formulas I are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the Formula I compounds which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties.

Examples of salts of compounds of Formula I include, for example, hydrochloride salts, methanesulfonic acid salts and trifluoroacetic acid salts. In addition, pharmaceutically acceptable salts of the Formula I compounds may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The present invention also encompasses a pharmaceutical composition useful in the treatment of cancer, comprising the administration of a therapeutically effective amount of the combinations of this invention, with or without pharmaceutically acceptable carriers or diluents. The pharmaceutical compositions of this invention comprise an anti-proliferative agent or agents, a formula I compound, and a pharmaceutically acceptable carrier. The methods entail the use of a neoplastic agent in combination with a Formula I compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, Formula I compounds and compositions of the present invention may be administered orally or parenterally including the intravenous, intramuscular, intraperitoneal, subcutaneous, rectal and topical routes of administration.

For oral use, the antineoplastic agents, Formula I compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of Formula I, as well as the anti-neoplastic agents, described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the combination compositions of this invention are employed within the dosage ranges described below. Alternatively, the anti-neoplastic, and Formula I compounds may be administered separately in the dosage ranges described below. In a preferred embodiment of the present invention, the antineoplastic agent is administered in the dosage range described below following administration of the Formula I compound in the dosage range described below.

Table I sets forth preferred chemotherapeutic combinations and exemplary dosages for use in the methods of the present invention. Where "Compound of Formula I" appears, any of the variations of Formula I set forth herein are contemplated for use in the chemotherapeutic combinations. For example, Compound 1 may be employed.

TABLE 1

| CHEMOTHERAPEUTIC COMBINATION | DOSAGE mg/m$^2$ (per dose) |
|---|---|
| Compound of Formula I + | 0.1–100 mg/m2 |
| Cisplatin | 5–150 mg/m2 |
| Compound of Formula I + | 0.1–100 mg/m2 |
| Carboplatin | 5–1000 mg/m2 |
| Compound of Formula I + | 0.1–100 mg/m2 |
| Radiation | 200–8000 cGy |
| Compound of Formula I + | 0.1–100 mg/m2 |
| CPT-11 | 5–400 mg/m2 |
| Compound of Formula I + | 0.1–100 mg/m2 |
| Paclitaxel | 40–250 mg/m2 |
| Compound of Formula I + | 0.1–100 mg/m2 |
| Paclitaxel + | 40–250 mg/m2 |
| Carboplatin | 5–1000 mg/m2 |
| Compound of Formula I + | 0.1–100 mg/m2 |
| 5FU and optionally + | 5–5000 mg/m2 |
| Leucovorin | 5–1000 mg/m2 |
| Compound of Formula I + | 0.1–100 mg/m2 |
| Epothilone | 1–500 mg/m2 |
| Compound of Formula I + | 0.1–100 mg/m2 |
| Gemcitabine | 100–3000 mg/m2 |
| Compound of Formula I + | 0.1–100 mg/m2 |
| UFT and optionally + | 50–800 mg/m2 |
| leucovorin | 5–1000 mg/m2 |
| Compound of Formula I + | 0.1–100 mg/m2 |
| Gemcitabine + | 100–3000 mg/m2 |
| Cisplatin | 5–150 mg/m2 |
| Compound of Formula I + | 0.1–100 mg/m2 |
| UFT + | 50–800 mg/m2 |
| Leucovorin | 5–1000 mg/m2 |
| Compound of Formula I + | 0.1–100 mg/m2 |
| Cisplatin + | 5–150 mg/m2 |
| paclitaxel | 40–250 mg/m2 |
| Compound of Formula I + | 0.1–100 mg/m2 |
| Cisplatin + | 5–150 mg/m2 |
| 5FU | 5–5000 mg/m2 |
| Compound of Formula I + | 0.1–100 mg/m2 |
| Oxaliplatin + | 5–200 mg/m2 |
| CPT-11 | 4–400 mg/m2 |
| Compound of Formula I + | 0.1–100 mg/m2 |
| 5FU + | 5–5000 mg/m2 |
| CPT-11 and optionally + | 4–400 mg/m2 |
| leucovorin | 5–1000 mg/m2 |
| Compound of Formula I + | 0.1–100 mg/m2 |
| 5FU + | 5–5000 mg/m2 |
| radiation | 200–8000 cGy |
| Compound of Formula I + | 0.1–100 mg/m2 |
| radiation + | 200–8000 cGy |
| 5FU + | 5–5000 mg/m2 |
| Cisplatin | 5–150 mg/m2 |
| Compound of Formula I + | 0.1–100 mg/m2 |
| Oxaliplatin + | 5–200 mg/m2 |
| 5FU and optionally + | 5–5000 mg/m2 |
| Leucovorin | 5–1000 mg/m2 |
| Compound of Formula I + | 0.1–100 mg/m2 |
| paclitaxel + | 40–250 mg/m2 |
| CPT-11 | 4–400 mg/m2 |
| Compound of Formula I + | 0.1–100 mg/m2 |
| paclitaxel + | 40–250 mg/m2 |
| 5-FU | 5–5000 mg/m2 |
| Compound of Formula I + | 0.1–100 mg/m2 |
| UFT + | 50–800 mg/m2 |
| CPT-11 and optionally + | 4–400 mg/m2 |
| leucovorin | 5–1000 mg/m2 |

In the above Table I, "5FU" denotes 5-fluorouracil, "Leucovorin" can be employed as leucovorin calcium, "UFT" is a 1:4 molar ratio of tegafur:uracil, and As an example, "epothilone" is a compound described in WO 99/02514 or WO 00/50423, both of which are incorporated by reference herein in their entirety.

While Table I provides exemplary dosage ranges of the Formula I compounds and certain anticancer agents of the invention, when formulating the pharmaceutical compositions of the invention the clinician may utilize other dosages as warranted by the condition of the patient being treated. For example, when Compound 1 is administered in combination with carboplatin, Compound 1 may be administered at 5 mg/m$^2$ to 60 mg/m$^2$ every 3 weeks and dosages for carboplatin may be within the range of 5 mg/m$^2$ to 1000 mg/m$^2$ or an AUC of 0.5–8 mg/ml×min. (dosage calculated per Calvert formula; Calvert et al., J. Clin. Oncol., 1989, 7, 1748–1756), such as an AUC of 4–6 mg/ml×min.

A compound of Formula I may be administered as a 10-minute to 3-hour infusion, for example, as a 60-minute infusion. The anti-proliferative agent may be administered as a 5-minute to 2-hour infusion, for example, as a 30-minute infusion.

A compound of Formula I may be administered daily, weekly for 1–5 consecutive weeks, or every 2–5 weeks, for example, every 3 weeks. The compound of Formula I may also be administered in divided doses during each treatment cycle. For example, a compound of Formula I may be administered on day 1 and day 8 of the treatment cycle and repeated every 3 weeks.

The anti-proliferative agent may be administered daily, weekly for 1–5 consecutive weeks, or every 2–5 weeks, for example, every 3 weeks. For example, the anti-proliferative agent may be administered on day 1 of the treatment cycle and repeated every 3 weeks. The anti-proliferative agent may also be administered in divided doses during each treatment cycle.

A treatment cycle comprises that duration of time in which the desired doses (either single or split) of a compound of Formula I and an anti-proliferative agent are administered, before administration of these compounds is repeated in subsequent rounds of treatment. Thus, a patient may undergo several rounds of treatment, or treatment cycles, as determined necessary by the clinician or physician.

In one embodiment of the present invention, Compound 1 may be administered as a 60-minute infusion, 30-minutes prior to a 30-minute carboplatin infusion on day 1. This combination is administered every three weeks for at least one treatment cycle. A treatment cycle, which in this embodiment is 3 weeks in duration, comprises one round of chemotherapy using the compound of Formula I and the anti-proliferative agent. Treatment on this schedule may occur in, but is not limited to, four dose cycles. In another embodiment of the present invention, the dosage of Compound 1 is between 5 and 60 mg/m$^2$ and the dosage of carboplatin is between 5 and 1000 mg/m$^2$ or between AUC 4 and 8. In yet another embodiment of the present invention, the dosage of Compound 1 is between 25 and 50 mg/m$^2$ and the dosage of carboplatin is between 5 and 1000 mg/m$^2$ or between AUC 5 and 6.

As another example of the present invention, the doses of Compound 1 are split on days 1 and 8 with carboplatin being administered on day 1. This combination of agents is administered every three weeks for at least one treatment cycle. A treatment cycle in this case comprises administration of Compound 1 on days 1 and 8 with administration of carboplatin on day 1. This is followed by 2 weeks of no therapy where neither Compound 1 nor an anti-proliferative agent is administered. This 3-week period comprises one treatment cycle. Such treatment cycles are continued for as long as needed. In one embodiment of the present invention, the dosage of Compound 1 is between 5 and 60 mg/m$^2$ and the dosage of carboplatin is between 5 and 1000 mg/m$^2$ or between AUC 4 and 8 (dosage calculated per Calvert formula; Calvert et al., J. Clin. Oncol., 1989, 7, 1748–1756). In another embodiment of the present invention, the dosage of Compound 1 is between 15 and 30 mg/m$^2$ and the dosage of carboplatin is between 5 and 1000 mg/m$^2$ or between AUC 5 and 6.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

When employing the methods or compositions of the present invention, other agents used in the modulation of tumor growth or metastasis in a clinical setting, such as antiemetics, can also be administered as desired.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

The attending clinician or physician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but to encompass the entire subject matter defined by the claims.

EXAMPLES

Compounds:

The following designations are used to identify the test compounds throughout the examples:

Compound 1: [1S-1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (compound of Formula Ia).

Chemicals and Solutions:

Unless specified, chemicals and solutions used for the maintenance of cell culture were obtained from GIBCO/BRL. Sterile tissue culture ware was obtained from Corning, N.Y. All other reagents were from Sigma or Fisher at the highest grade available.

Drug Administration:

For administration of Compound 1 (an epothilone), two different excipients have been used: (1) ethanol/water (1:9, v/v) and (2) Cremophor®/ethanol/water (1:1:8, v/v). Compound 1 was first dissolved in ethanol or a mixture of Cremophor®/ethanol (50:50). Final dilution to the required dosage strength is made less than 1 h before drug administration. For parenteral administration (IV), dilution was made with water so that the dosing solutions contain the specified excipient composition described above.

Example 1

Pharmacological Studies of Compound 1 in Combination with Carboplatin in Patients with Advanced Cancer Compound 1 followed by carboplatin was given intravenously every 3 weeks to patients with advanced solid tumors treated with ≦2 prior chemotherapy regimens. Pharmacokinetics of both drugs were measured on the first course. Twenty-five (25) patients were treated at four dose levels—combining Compound 1 (30 or 40 mg/m$^2$) with 5–1000 mg/m$^2$ or AUC 5 or 6 (Calvert formula; Calvert et al., J. Clin. Oncol., 1989, 7, 1748–1756) of carboplatin. A total of 91 courses were given. Transient CTC grade 4 neutropenia was noted at all dose levels and was dose limiting at 40 mg/m$^2$/AUC 6 (2/2 patients with complicated grade 4 neutropenia). The major non-haematological toxicities were myalgia on day 4 and cumulative peripheral neuropathy. Seven patients withdrew from the trial because of neurotoxicity, grade 2/3 sensory neuropathy after at least 3 courses but grade 3 motor neuropathy in one patient on the first course. The regimen was active with 3/25 confirmed partial responses (breast, neuroendocrine and unknown primary carcinomas) and 12 patients have disease stabilization and clinical benefit from treatment.

The maximum tolerated dose of Compound 1 was 40 mg/m$^2$ with carboplatin AUC 5 (dosage calculated per Calvert formula, which allows determination of dosage based upon renal function of patient; Calvert et al., J. Clin. Oncol., 1989, 7, 1748–1756).

Example 2

Pharmacological Studies of Compound 1 in Combination with Carboplatin in Patients with Advanced Cancer Compound 1 was assessed in Phase I studies in combination with other chemotherapeutic agents. Compound 1 was given as a 60-minute infusion, 30 minutes prior to a 30-minute carboplatin infusion on day 1 every three weeks (or 21 days). Pharmacokinetic samples were taken during the first cycle. Twenty-five (25) patients were treated on this schedule at 4 dose levels (Compound 1 doses of 30 mg/m$^2$ or 40 mg/m$^2$ with carboplatin doses of 5–1000 mg/m$^2$, or AUC 5 or 6). Dose limiting toxicity (DLT) occurred with 40 mg/m$^2$ of Compound 1 and carboplatin AUC 6 (per Calvert formula) on this schedule, with myelosuppression as the major toxicity.

A further 14 patients were recruited onto an amended schedule with Compound 1 doses being split and administered on days 1 and 8 every three weeks (or 21 days) and carboplatin being administered on day 1. DLT on this schedule was observed with carboplatin AUC 6 and with Compound 1 at 25 mg/m$^2$ being administered on days 1 and 8. The preceding dose level (carboplatin AUC 6 and Compound 1 at 20 mg/m$^2$ on days 1 and 8) was expanded and a total of 8 patients were treated.

Thirty-nine (39) patients (18 male/19 female/2 missing) were treated over seven (7) dose level; 92% were WHO performance status 0 or 1 at entry; mean age 55 years (range 31–74). Fifty-six percent (56%) of patients had received prior chemotherapy (3 or fewer regimens) and 51% had prior radiotherapy. Major toxicities were myelosuppression, myalgia and peripheral neuropathy. Eleven patients withdrew from the study because of study drug toxicity, with peripheral neuropathy being reported in all these patients.

The regimen was active: partial responses were reported in five (5) patients (2 breast, neuro-endocrine, unknown primary carcinomas and mesothelioma), 48% of patients showed disease stabilization for more than two months. Analysis of Compound 1 plasma levels show that $C_{max}$ and AUC increase with dose, the volume of distribution is high and half-life is ~30 hours. Thus, Compound 1 can safely be combined with carboplatin, with the major toxicities being neutropenia and peripheral neuropathy. Dividing the dose of Compound 1 allows a higher dose intensity to be achieved.

What is claimed is:

1. A method of treating cancer in a patient comprising administering to the patient the compound which is [1S1R*,3R*(E),7R*, 10S*, 11R*, 12R*, 16S*]]-7, 11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (Compound 1), wherein Compound 1 is administered in a split dose, first on day 1 and then again on day 8, and carboplatin is administered on day 1, for at least one treatment cycle, wherein the cancer is selected from bladder cancer, pancreatic cancer, prostate cancer, lung cancer, colorectal cancer and breast cancer.

2. The method of claim 1 wherein said dose of [1S1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (Compound 1) on day 1 is administered as a 60-minute infusion, 30 minutes prior to a 30-minute infusion of carboplatin.

3. The method of claim 1 wherein the dosage of said [1S1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclol[14.1.0]heptadecane-5,9-dione (Compound 1) on day 1 and/or day 8 is between 5 mg/m$^2$ and 60 mg/m$^2$ and the dosage of carboplatin is between 5 mg/m$^2$ and 1000 mg/m$^2$.

4. The method of claim 3 wherein the dosage of said [1S1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (Compound 1) on day 1 and/or day 8 is between 15 and 30 mg/m² and the dosage of carboplatin is between 5 mg/m² and 1000 mg/m².

5. The method of claim 1, wherein the cancer is breast cancer.

6. The method of claim 1, wherein the cancer is non small-cell lung cancer.

7. The method of claim 1, wherein the cancer is prostate cancer.

8. A method of treating cancer in a patient comprising administering to the patient the compound which is [1S1R*, 3R*(E),7R*,10S*,11R*,12R*,16S*]]-7,11-dihydroxy-8,8, 10,12,16-pentamethyl-3-[1-methyl-2-(2-methyl-4-thiazolyl) ethenyl]-4-aza-17-oxabicyclo[14.1.0]heptadecane-5,9-dione (Compound 1), wherein Compound 1 is administered in a split dose, first on day 1 and then again on day 8, and carboplatin is administered on day 1, for at least one treatment cycle, wherein the cancer is refractory to taxane treatment.

* * * * *